(12) United States Patent
Hostetler

(10) Patent No.: US 7,296,464 B2
(45) Date of Patent: Nov. 20, 2007

(54) UNDERWATER SAMPLING AND MAPPING APPARATUS

(76) Inventor: Paul Blair Hostetler, 5 Marshall Avenue, Warrawee, New South Wales, 2074 (AU)

( * ) Notice: Subject to any disclaimer, the term of this patent is extended or adjusted under 35 U.S.C. 154(b) by 98 days.

(21) Appl. No.: 10/480,072

(22) PCT Filed: Jun. 7, 2002

(86) PCT No.: PCT/AU02/00743

§ 371 (c)(1),
(2), (4) Date: Aug. 31, 2004

(87) PCT Pub. No.: WO02/100715

PCT Pub. Date: Dec. 19, 2002

(65) Prior Publication Data

US 2005/0034509 A1 Feb. 17, 2005

(30) Foreign Application Priority Data

Jun. 8, 2001 (AU) .................................. PR5600

(51) Int. Cl.
*G01P 13/00* (2006.01)
(52) U.S. Cl. .................. 73/170.33; 73/53.01
(58) Field of Classification Search ............... 73/53.01, 73/863, 864, 170.33, 170.29
See application file for complete search history.

(56) References Cited

U.S. PATENT DOCUMENTS

| | | | | |
|---|---|---|---|---|
| 3,147,431 A | * | 9/1964 | Bennett et al. ............. | 324/706 |
| 3,652,439 A | * | 3/1972 | Ben-Yaakov et al. ....... | 204/408 |
| 3,747,405 A | * | 7/1973 | Fort et al. ................. | 73/170.33 |
| 3,780,220 A | * | 12/1973 | Fugitt et al. ................ | 348/81 |
| 3,841,156 A | * | 10/1974 | Wolfe .......................... | 73/291 |
| 4,175,432 A | * | 11/1979 | Gibson ..................... | 73/170.33 |
| 4,658,750 A | | 4/1987 | Malcosky | |

(Continued)

FOREIGN PATENT DOCUMENTS

DE 195 04 392 A1 1/1996

(Continued)

OTHER PUBLICATIONS

Derwent Abstract Accession No. 88-262640/37, SU 1376997A, *SKRIPKIN*, Feb. 29, 1988.

(Continued)

*Primary Examiner*—Hezron Williams
*Assistant Examiner*—Paul M West
(74) *Attorney, Agent, or Firm*—Christensen O'Connor Johnson Kindness PLLC

(57) ABSTRACT

The present application provides a system, method and apparatus for measuring at least one physical and/or chemical variable at a plurality of different locations within a body of water. The method includes the steps of: providing dynamic measurement means configured to measure the at least one physical and/or chemical variable; towing said measurement means in said body of water at a predetermined depth, and simultaneously taking measurements of least one physical and/or chemical variable, at least periodically, and generating measurement data; and determining the location of the measurement means while taking said measurements of the at least one physical and/or chemical variable and generating corresponding location data. A method for mapping at least one physical and/or chemical variable for a body of water is also disclosed.

36 Claims, 6 Drawing Sheets

U.S. PATENT DOCUMENTS 4,713,967 A * 12/1987 Overs et al. .............. 73/170.33
5,438,552 A *  8/1995 Audi et al. .................... 367/88
5,441,638 A     8/1995 Tillich
5,570,303 A * 10/1996 Dessureault ............. 73/170.33
6,536,272 B1 *  3/2003 Houston et al. ......... 73/170.29

FOREIGN PATENT DOCUMENTS

| | | |
|---|---|---|
| EP | 0 572 998 A2 | 12/1993 |
| JP | 10150418 A | 6/1998 |
| RU | 2070130 C1 | 12/1996 |

OTHER PUBLICATIONS

Derwent Abstract Accession No. 92-149109/18, SU 16652265A, *Oceanology Inst*, Jul. 23, 1991.

* cited by examiner

UNDERWATER SAMPLING AND MAPPING APPARATUS

CROSS-REFERENCE TO RELATED APPLICATION

The application is a national stage application of prior International Application No. PCT/AU02/00743, filed Jun. 7, 2002, which claims the benefit of Australian application No. PR5600, filed Jun. 8, 2001, which are incorporated herein by reference.

FIELD OF THE INVENTION

The present invention relates to a method and apparatus for performing multi-variable mapping of bodies of surface water.

BACKGROUND OF THE INVENTION

It is now clear that human activity can have a great impact on the environment. As a result of this realisation, an environmental impact statement or environmental assessments are often made before a development is begun. The appreciation of the potential for human impact on the environment may also lead to an increase in research and environmental modelling in order to determine the, mechanisms for, and effects of, human activity on the environment.

In order to increase the speed, quality, accuracy and cost effectiveness of environmental assessment, environmental monitoring and base line surveying improved techniques and systems for measuring physical variable in the environment are desired.

SUMMARY OF THE INVENTION

According to a first aspect of the present invention there is provided a method for measuring at least one physical and/or chemical variable at a plurality of different locations within a body of water, said method including the steps of:

providing dynamic measurement means configured to measure the at least one physical and/or chemical variable;

towing said measurement means in said body of water at a predetermined depth, and simultaneously taking measurements of least one physical and/or chemical variable, at least periodically, and generating measurement data; and determining the location of the measurement means while taking said measurements of the at least one physical and/or chemical variable and generating corresponding location data.

Preferably the method includes the additional the step of:

controlling the depth of the measurement means in said body of water whilst towing said measurement means.

Preferably the method includes the additional the step of:

detecting obstacles in a region adjacent to said measurement means; and wherein the step of controlling the depth of said measurement means is performed in response to detected obstacles.

Preferably the step of, detecting obstacles in a region adjacent to said measurement means, includes the sub-steps of:

providing image capture means on said measurement means, adapted to generate a sequence of images of a region adjacent to said measurement means; and visually detecting said obstacles from said sequence of images.

Preferably said measurement means includes water intake means configured to collect water from said body of water and wherein said method includes the additional step of:

collecting at least one water sample from said body of water through said water intake means.

Preferably the predetermined depth is determined relative to a bottom of the body of water.

Preferably water depth and at least one other physical and/or chemical variable is measured by said measurement means.

Preferably the at least one physical and/or chemical variable measured by the measurement means is selected from a list including the following physical and chemical variables:

water depth, water temperature, conductivity, and water turbidity, pH, dissolved oxygen, dissolved chloride, oxidation-reduction potential (ORP), soluble nitrate, ammonia, dissolved gases or chlorophyll A.

According to a second aspect of the present invention there is provided a method of mapping at least one physical and/or chemical variable in body of water, said method including the steps of:

providing dynamic measurement means configured to measure the at least one physical and/or chemical variable; and towing said measurement means in said body of water at a predetermined depth, and simultaneously taking measurements of said at least one physical and/or chemical variable, at least periodically, and generating measurement data;

determining the location of the measurement means while taking said measurements of the at least one physical and/or chemical variable and generating corresponding location data; and generating a map representative of the distribution of the at least one physical and/or chemical variable within said body of water on the basis of the location and measurement data.

Preferably the method additionally includes the additional the step of:

determining the depth of the measurement means when measuring said at least one physical and/or chemical variable, and generating measurement depth data, and wherein said map is generated on the basis of the measurement depth data, measurement data and location data.

Preferably the method includes the additional the step of:

controlling the depth of the measurement means in said body of water whilst towing said measurement means.

Preferably the method includes the additional the step of:

detecting obstacles in a region adjacent to said measurement means; and wherein the step of controlling the depth of said measurement means is performed in response to detected obstacles.

Preferably the step of, detecting obstacles in a region adjacent to said measurement means, includes the sub-steps of:

providing image capture means on said measurement means, adapted to generate a sequence of images of a region adjacent to said measurement means; and visually detecting said obstacles from said sequence of images.

Preferably said measurement means includes water intake means configured to collect water from said body of water and wherein said method includes the additional step of:

collecting at least one water sample from said body of water through said water intake means.

Preferably the predetermined depth is determined relative to a bottom of the body of water.

Preferably water depth and at least one other physical and/or chemical variable is measured by said measurement means.

Preferably the at least one physical and/or chemical variable measured by the measurement means is selected from a list including the following physical and chemical variables:

water depth, water temperature, conductivity, and water turbidity, pH, dissolved oxygen, dissolved chloride, oxidation-reduction potential (ORP), soluble nitrate, ammonia, dissolved gases or chlorophyll A.

Preferably the map represents topographic contours of a bottom of the body of water and the distribution of the at least one physical and/or chemical variable within said body of water.

According to a third aspect of the present invention there is provided measurement means configured to measure at least one physical and/or chemical variable in a body of water, said measurement means including, a housing, and at least one sensor mounted at least partially within said housing, said sensor being configured to measure at least one physical and/or chemical variable, wherein said measurement means is configured to be towed in said body of water at a predetermined depth whilst simultaneously measuring, at least periodically, said least one physical and/or chemical variable.

The measurement means can further include orientation means configured to orientate said measurement means relative to an apparent current experienced by said measurement means when said measurement means is being towed. Preferably said orientation means includes at least one fin.

The measurement means can further include water intake means to allow the collection of a sample of water from the body of water.

The measurement means can further include image capture means adapted to generate a sequence of images of a region of said body of water adjacent to said measurement means, wherein in use the depth of the measurement means is controlled in response to the sequence of video images.

Preferably the at least one sensor is configured to measure one or more of the following physical and chemical variables:

water depth, water temperature, conductivity, water turbidity, pH, dissolved oxygen, dissolved chloride, oxidation-reduction potential (ORP), soluble nitrate, ammonia, dissolved gases or chlorophyll A.

Preferably there is more than one sensor. Each sensor can measure one or more physical and/or chemical variables.

Preferably said housing includes a frame.

Preferably said housing includes a water permeable container configured to contain said at least one sensor.

The measurement means can further include data storage means in communication with said at least one sensor, said data storage means being configured to store measurement data generated by said at least one sensor.

According to a fourth aspect of the present invention there is provided a system for taking a series of measurements of at least one physical and/or chemical variable in a body of water, said system including:

measurement means configured to measure at least one physical and/or chemical variable in a body of water, wherein in use said measurement means is configured to be towed in said body of water at a predetermined depth whilst simultaneously measuring, at least periodically, said at least one physical and/or chemical variable to generate measurement data; and location means configured to determine the location of the measurement means while taking said measurements of the at least one physical and/or chemical variable to generate location data; and data storage means configured to store said measurement data and location data.

Preferably the system includes depth control means configured to control the depth of the measurement means while said measurement means is being towed.

Preferably the system includes image capture means adapted to provide a sequence of images of a region of the body of water adjacent the measurement means.

Preferably the system includes water inlet means, mounted on said measurement means, configured to allow collection one or more water samples from the body of water.

Preferably the at least one measurement means is configured to measure one or more of the following physical or chemical variables:

water depth, water temperature, conductivity, water turbidity, pH, dissolved oxygen, dissolved chloride, oxidation-reduction potential (ORP), soluble nitrate, ammonia, dissolved gases or chlorophyll A.

The present invention also provides a dataset including a plurality of measurements obtained according to the method described above, and a map representing such a dataset.

The present invention additionally provides a map generated according to the mapping method of described above.

BRIEF DESCRIPTION OF THE DRAWINGS

Notwithstanding any other forms which may fall within the scope of the present invention, preferred forms of the invention will now be described, by way of example only, with reference to the accompanying drawings in which.

DETAILED DESCRIPTION OF THE EMBODIMENTS

Figure 1A:
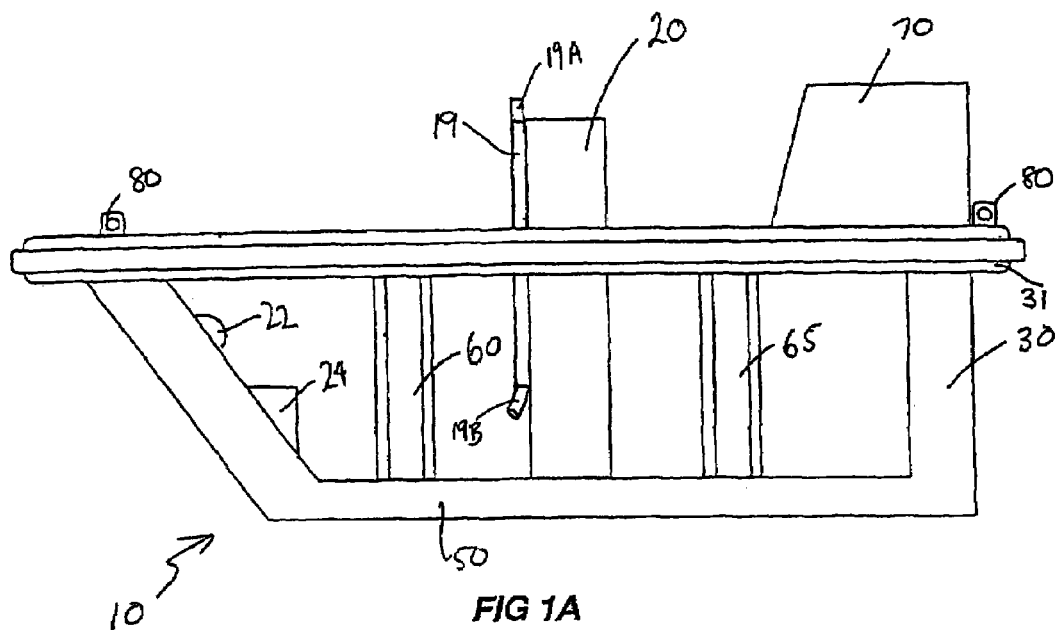
FIG. 1A shows the side view of an apparatus according to an embodiment of the present invention.
Figure 1B:
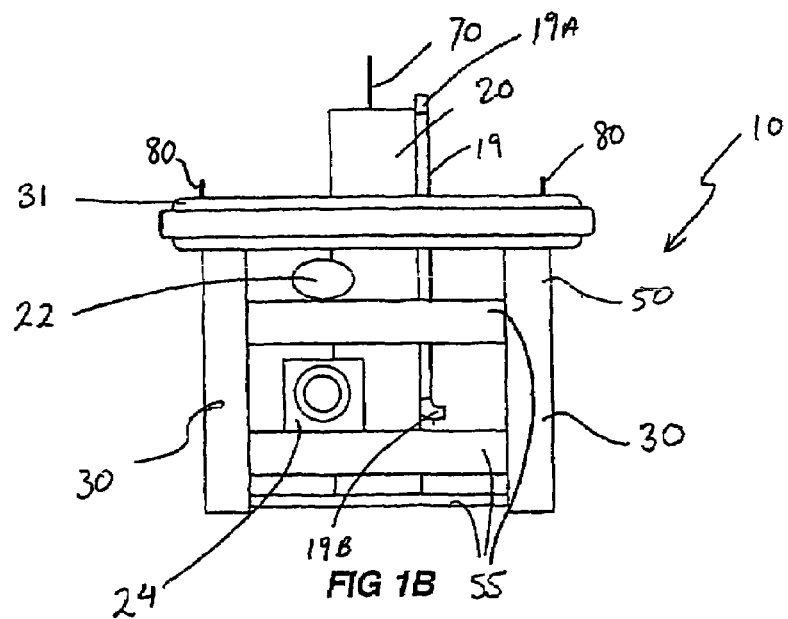
FIG. 1B shows a front view of the apparatus shown in FIG. 1A.

FIG. 1A shows a side view of an measurement means or instrument pack 10 which is adapted to be towed underneath a boat in a body of surface water, such as a lake, in order to take measurements of one or more water quality variables. The instrument pack or sled 10 includes of an instrument housing, or stack 20, which is centrally mounted within a supporting frame 50. The frame 50 comprises a pair of vertically mounted generally trapezoidal outer frames 30 with a horizontally disposed rectangular frame member 31 along its top side. The frame 50 additionally includes vertically and horizontally disposed support members 60, 65 and 55 respectively to provide additional strength to the frame 50. FIG. 1B, which depicts a front view of the sled 10, shows the horizontal support members 55 spaced between the pair of trapezoidal frame members 30.

The sled 10 additionally includes a fixed rudder 70, which comprises a vertically oriented generally flat plate. The rudder 70 acts as a vane to orientate the sled 10 when in use. The sled 10 additionally includes a plurality of lifting eyes 80 from which the sled 10 is suspended when in use.

The sled 10 is adapted to carry various sensors and instruments which can be used to map bodies of surface water. The stack 20 comprises a cylinder of perforated PVC pipe inside which is housed one or more sensors used by the measurement means to take measurement of physical or chemical variables. In a preferred embodiment the sensor(s) loosely mounted within the stack 20 to provide shock absorption. Further shock protection for the sensor(s) can be provided by a layer of protective padding, such as foam rubber or the like, which can be mounted between the sensor(s) and the inner wall of the stack 20.

Sensors can be provided which measure parameters such as water depth, water temperature, pH, dissolved oxygen, dissolved chloride, conductivity, oxidation-reduction potential and water turbidity. A suitable sensor for measuring each of these parameters is manufactured by the Hydro Lab Corporation of Austin, Texas. An integrated unit, known as the "Sonde", contains the sensors for each of the above mentioned parameters. However, it will be appreciated by a person skilled in the art that other suitable sensors are available, and many other water quality, or physical variables can be measured.

In addition to the stack 20, which houses the sensors the sled 10 has mounted on it a lamp 22 and video camera 24, which both face in generally forward direction. Preferably, the lamp illuminates an ark of around 120 degrees and produces illumination of sufficient intensity to produce a visibility of 6 meters or more at a water depth of 50 meters.

Additionally, a section of hose 19 or pipe is mounted adjacent to the stack. The hose 19 has a valve 19B at its bottom end and a connection means 19A at its top end. In the use, the hose segment 19 is connected to a pump and filter system via a main hose or conduit (not shown), and can be used to pump water to the surface from adjacent the sensors, in order to take water samples.

Figure 2:
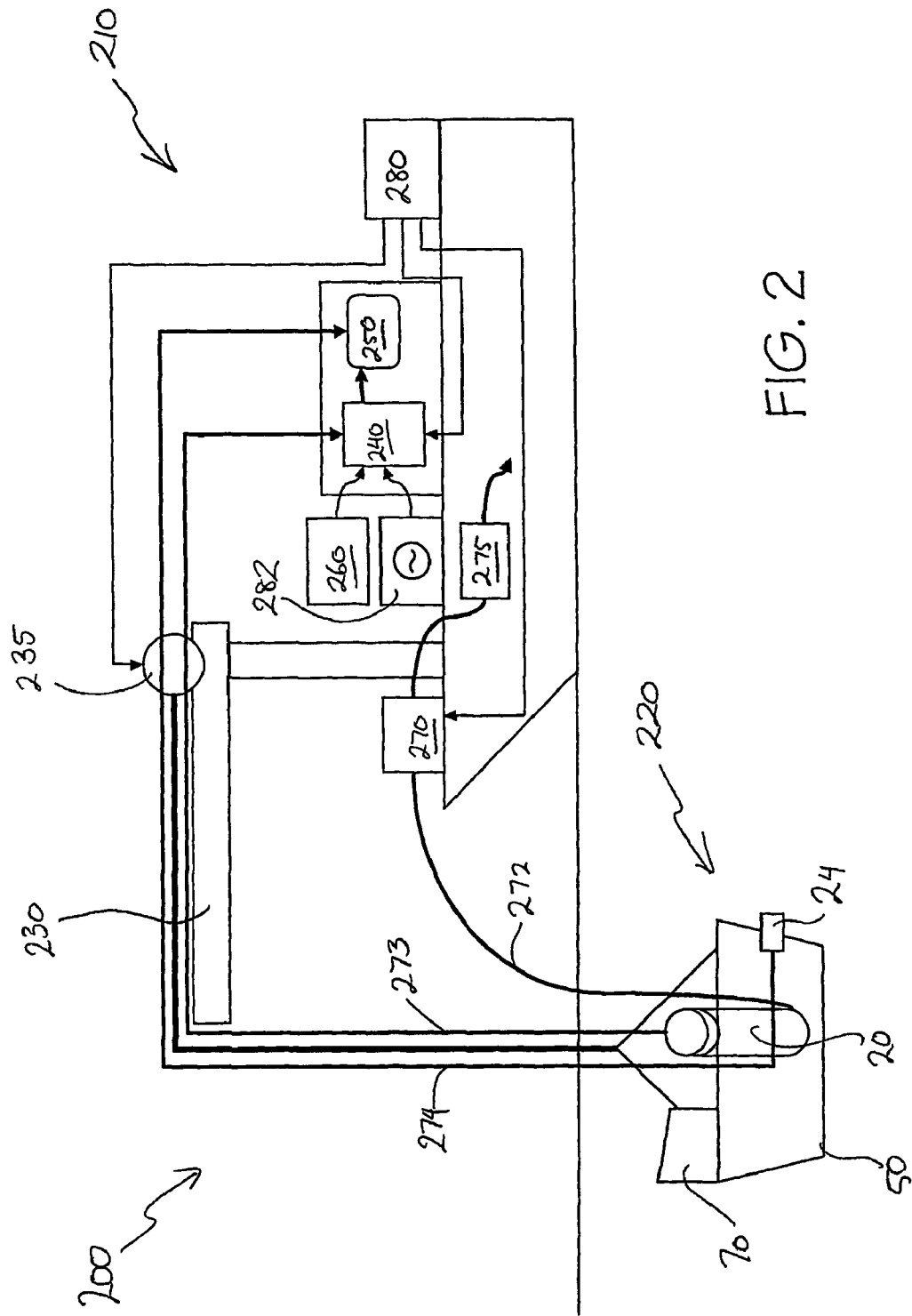
FIG. 2 shows a schematic representation of a system adapted to perform a method according to an embodiment of the present invention.
Figure 3:
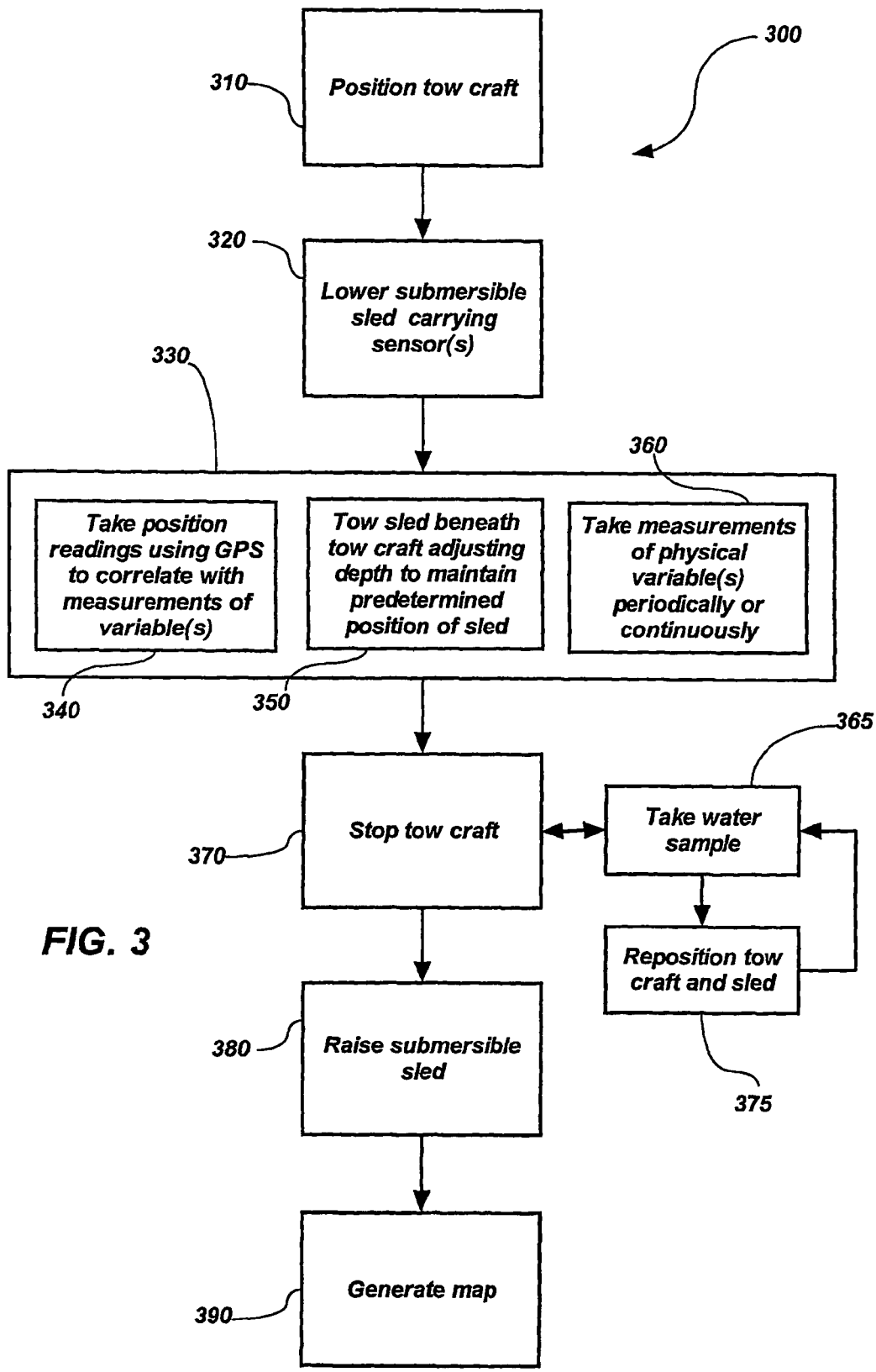
FIG. 3 shows a flowchart depicting a method of mapping a body of water according to an embodiment of the present invention.

Turning now to FIG. 2 which shows an exemplary embodiment of a system including a sled 10 as described above, adapted to take measurements and/or generate multi-variable maps of a body of surface water.

The system 200 is comprised of two portions. The first, or on board portions 210 comprises all necessary equipment required to record and track data produced by the sensors, collect water samples, and allow practical operation of the system. The so called "on board" portion 210 of the system 200 is thus named as it is generally mounted on board a vessel such as a boat, or barge, or the like.

The second portion, termed the "under water portion" 220 is comprised of the sled, sensors and monitoring equipment mounted thereon, as described in connection with FIGS. 1A and 1B.

Turning now to the on board portion, 210 of the system 200. The on board components 210 include the following equipment:

A boom winch 230. The boom winch 230 is used to raise and lower the sled 220 as required. Preferably, the boom winch is adapted to lift the sled entirely clear of the water and on board the tow vessel, where the sled can be securely stowed.

Winch drive 235. The winch drive 235 is of a commonly known type and acts to reel in the sled via the boom 230.

A data acquisition system 240. The data acquisition system collects and records data from the sensors mounted on the sled, and additionally stores navigation information such as the tow boat's position and other appropriate parameters such as the time a reading is taken. The data acquisition system 240 will in general be a computer including a central processing unit and data storage device.

A video monitor 250. The video monitor 250 displays images captured by the camera mounted on the sled 220. The images displayed on the monitor are used by the system operator to ensure that the sled does not collide with any objects in its path and to ensure that the sled is maintained at a suitable separation from the floor of the body of surface water being mapped. Additionally, the images captured by the camera can be recorded for later visual analysis of the floor of the body of surface water being mapped if required.

Navigation DGPS 260. A differential global positioning system (DGPS) and antenna is mounted on the tow vehicle to provide accurate monitoring of the path of the tow vehicle. The data from the navigation DGPS 260 is sent to the data acquisition system and recorded along side simultaneously taken measurements of one or more water quality variables to generate a data set.

Pump 270 and filter 275. The pump 270 and filter 275 are used to obtain samples of water from a position along side the sled. The pump 270 is kept in fluid communication with the sled via a conduit hose 272. In order to obtain a sample the pump is activated and water is pumped from the sampling site. Prior to collection as a sample the water is filtered to remove any large particles using filter 275. In order to avoid having to prime the pump before each sample is taken a foot valve is located on the bottom most end of pipe 272 to maintain a column of water within the pipe 272.

Generators 280 and 282. Generators 280 and 282 provide the required electrical power for the various on board components and under water components of the system 200. In the embodiment shown in FIG. 2 two separate generators 280, 282 are shown, first being a 240 volt AC generator 282 for suppling power to the data acquisition system and video monitor, and the second being a twelve volt DC generator 280 for suppling power to the boom winch 230 and the pump 270.

The operation of a system of the type disclosed in FIG. 2 in a process for taking a series of measurements of one or more water quality variables, and the creation of a map plotting such water quality variable will now be described in connection with FIGS. 3 to 6.

In a first step 310 of the method 300 the tow craft is maneuvered to a suitable position on the body of water to be mapped, to begin collecting data of the physical variable of interest. The tow craft will typically be a speedboat or barge, or the like, and will have mounted on it the "on board" components 210 of the system of FIG. 2. Initially the tow craft additionally carries the sled 220 and associated sensors and monitoring devices as described above. Once the tow craft is in position the sled 220 can be lowered, in step 320, into the water using boom winch 230 to a position as shown in FIG. 2. The sled 220 is in communication with the data acquisition 240 and video monitor 260 of the system 200 via data cables, 273, 274 respectively. Fluid communication with pump 270 is maintained via conduit 272 so that water samples can be taken as required.

In most applications a predetermined vertical position in the lake will be chosen, at which to take measurements of the variable of interest. For example, if the chosen vertical position is a this may be at a particular depth, say ten meters, the results obtained and map produced will show a horizontal cross-section of a variable in the lake at the chosen depth. Alternatively, the vertical positioning of the sled may be determined with reference to the bottom of the body of water for example measurements can be taken adjacent the bottom of the body of water. In such a situation, the sled 220 is lowered until it is adjacent to, but not touching the bottom of the body of water. It has been found that measurements of the concentration of various substances or physical variable at the bottom of a body water can be measured by maintaining a separation of approximately one meter between the sled and the bottom of the body of water.

Once the sled 220 is submerged to the desired depth the data collection process 330 can be begun. The data collection process 330 includes three processes, which are preformed substantially simultaneously.

In the data collection process 330 the sled 220 is towed beneath the tow craft, such that the predetermined vertical position of the sled is maintained (step 350). If measurements are to be taken at a particular depth no adjustment of the depth of the sled will be required, unless an obstacle is encountered during the measurement run. However, if the sled is to be maintained a set distance, say one meter, above the floor of the body of the water the boom winch (230 of FIG. 2) is used to raise and lower the sled 220 such that the desired separation between the sled and the floor of the body of water is maintained. In order to allow the sled 220 to be maintained at the correct vertical position using the boom winch, (230 of FIG. 2) video images from a camera mounted on sled 220 are displayed on a monitor 250. The person operating the winch drive 235 is able to view the region of the body of water adjacent to the sled 10 and operate the boom winch to raise the sled 220 clear of any obstacles in its path, or lower the sled so that the desired separation between the sled and the floor of the body of water is maintained.

It should be noted that the fixed rudder (feature 70 of FIGS. 1A and 1B) acts to orientate the sled 220 such that the front of the sled 220 always points in an "upstream" direction, that is in the direction of travel of the sled and tow craft, if no current is present, or into the perceived water flow, if a cross current acts on the sled. By ensuring correct orientation of the sled, the video camera mounted on the sled always points in the direction of motion of the sled, thereby allowing the driver of the boom winch to see any obstacles as the sled approaches them.

In order to allow the winch driver sufficient time to lift the sled clear of any obstacles in its way, the tow craft should tow the sled at a suitable speed. If the tow speed is too high there is a danger that the boom winch will not be able to raise the sled quickly enough in order to clear any obstacles in its path. If the tow speed is too low a non-optimal amount of data will be collected during a tow run. Additional parameters which affect the optimal speed at which to tow the sled include, the time required for the sensors mounted on the sled 220 to reach equilibrium with the surrounding water, and the need to maintain a sufficient correlation between the position of the sled and the towing craft. If a high tow speed is used the sled will lag behind the tow craft by a greater distance and the position of the boat determined by the DGPS system will not be representative of the position of the sled 220. By adding ballast to the sled 10 the distance the sled lags behind the tow craft towed can be reduced. Thus in areas of high current ballast can be added to the sled ensure that the sled 10 is not swept too far away from the tow-craft. If the current is relatively slow unnecessary ballast can be removed.

As will also be appreciated by a person skilled in the art the sled should be towed slowly enough for its sensors to come into equilibrium with the surrounding water before making each measurement, otherwise accurate measurements of water quality variable will not be achieved. Typically a speed of around 2 km/h is suitable for taking measurements.

With the sled being towed at the desired depth, measurements of water quality can be taken (step 360.) Preferably, measurements of more than one water quality variable are taken simultaneously. In step 340 the position of the tow craft is determined using the global positioning system, thus producing a data set representing the measurement location and one or more water quality variable. This process can be repeated, thereby building up a data set of water quality measurements and corresponding position readings.

At any particular point of interest the tow craft may be stopped (step 370) and water samples taken from the site. The water samples are taken by using pump 272 to pump water up conduit 272 and through a filter, prior to collection. Advantageously conduit 272 attaches to a length of hose (e.g. 19A of FIG. 1) on the sled which is fitted with a foot valve 19B, thereby allowing a column of water to be maintained in the conduit 272, and removing the need to prime pump 272 before taking each water sample. Once a water sample is taken (step 365) the tow craft and sled can be repositioned and further water samples taken (step 375.) This process may be repeated either during the measurement run (process 330) or separately.

Once all measurements are taken the sled 380 can be lifted out of the water and back into, a stowed position on the tow craft (step 380.)

At this point all of the data has been collected and a map can be generated (step 390) using suitable computer software. Preferably, a topographic map is overlain onto the region being surveyed. Typically a map of the area which has been surveyed has overlayed on to it, in contrasting colours, additional contours or regions shaded to depict the concentration, intensity or variation in the measured physical or chemical variable. It is preferable that the topographic information is derived from water depth readings from the measurement means. However other sources such as the towing boat's depth finder or even available hydrographic charts can be used to obtain the necessary topographical information.

As discussed above a system and method according to the present invention, can accumulate data along the bottom of a body of water, at intermediate depth in the body of water, or along lines of constant bearing. Existing software programs are available (such as "Surfer") which are adapted to translate data so collected into contour maps, cross-section maps, three dimensional maps or correlation graphs of two or more of the measured variable. Maps and graphs may also be prepared based on the analysis of water samples taken during a sampling run.

Figure 4:
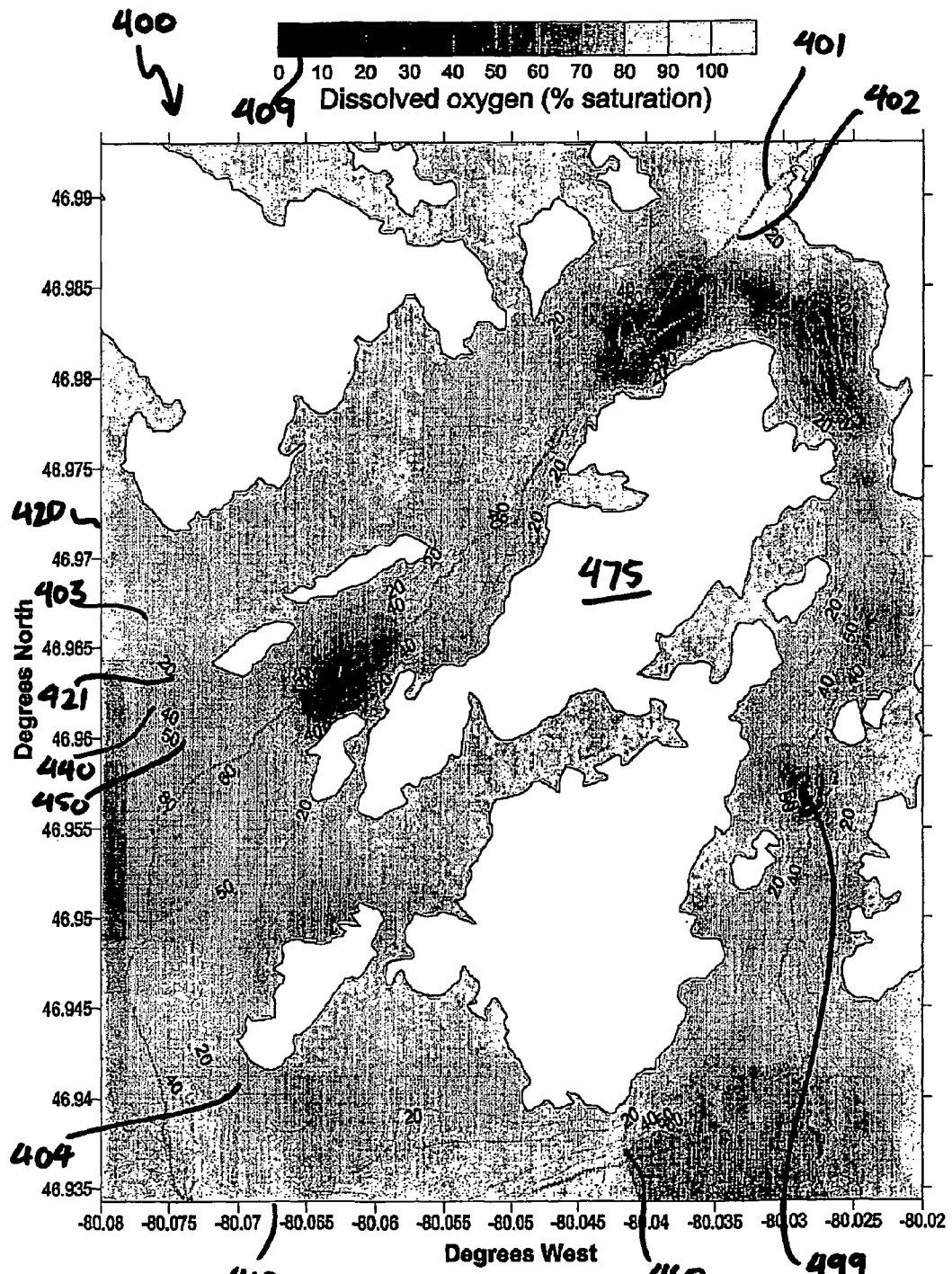
FIG. 4 shows a map of a lake created from an exemplary output of the system, showing bottom depth contours vs. dissolved oxygen contours.
Figure 5:
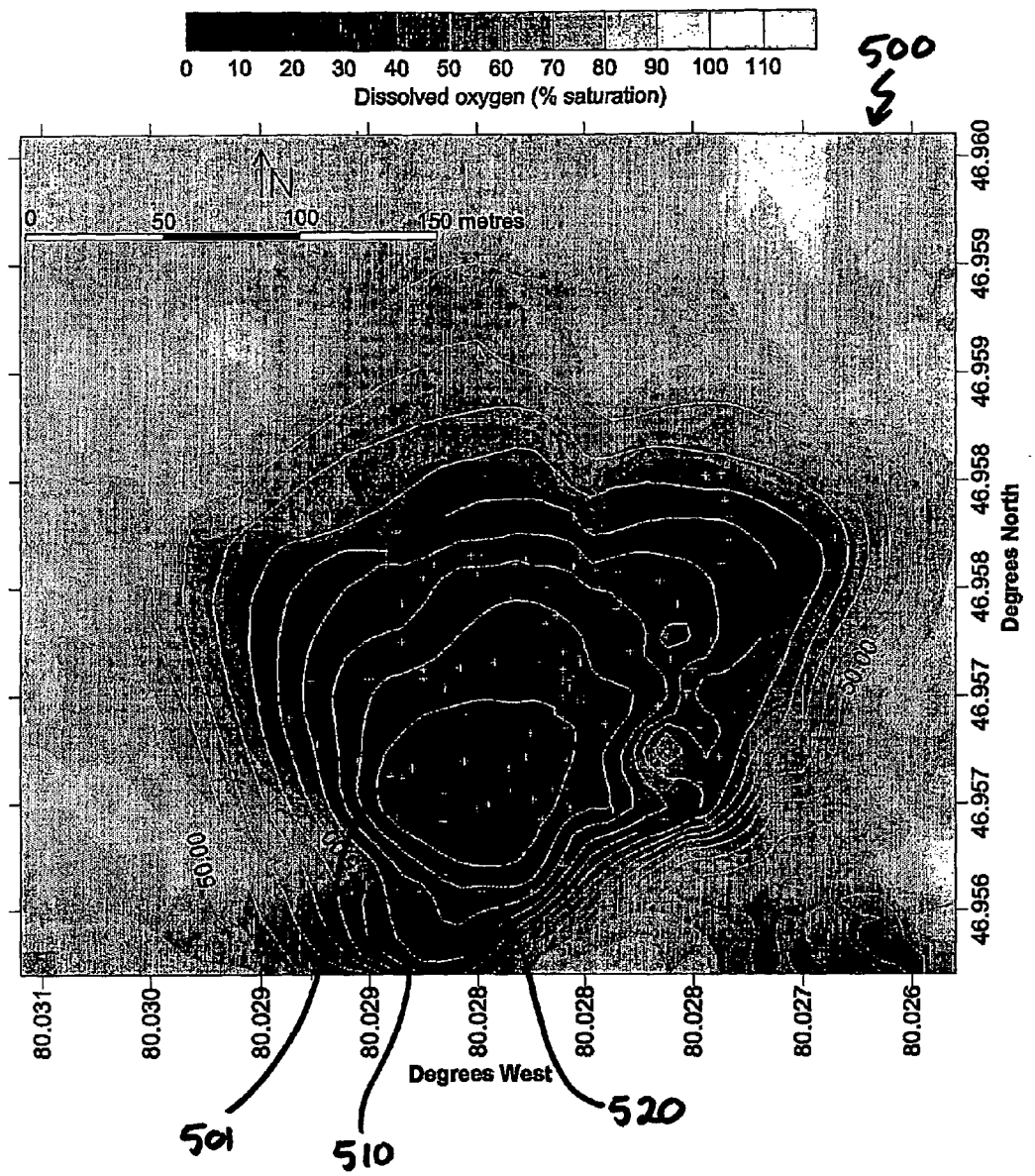
FIG. 5 shows a closer view of a region of FIG. 4.
Figure 6:
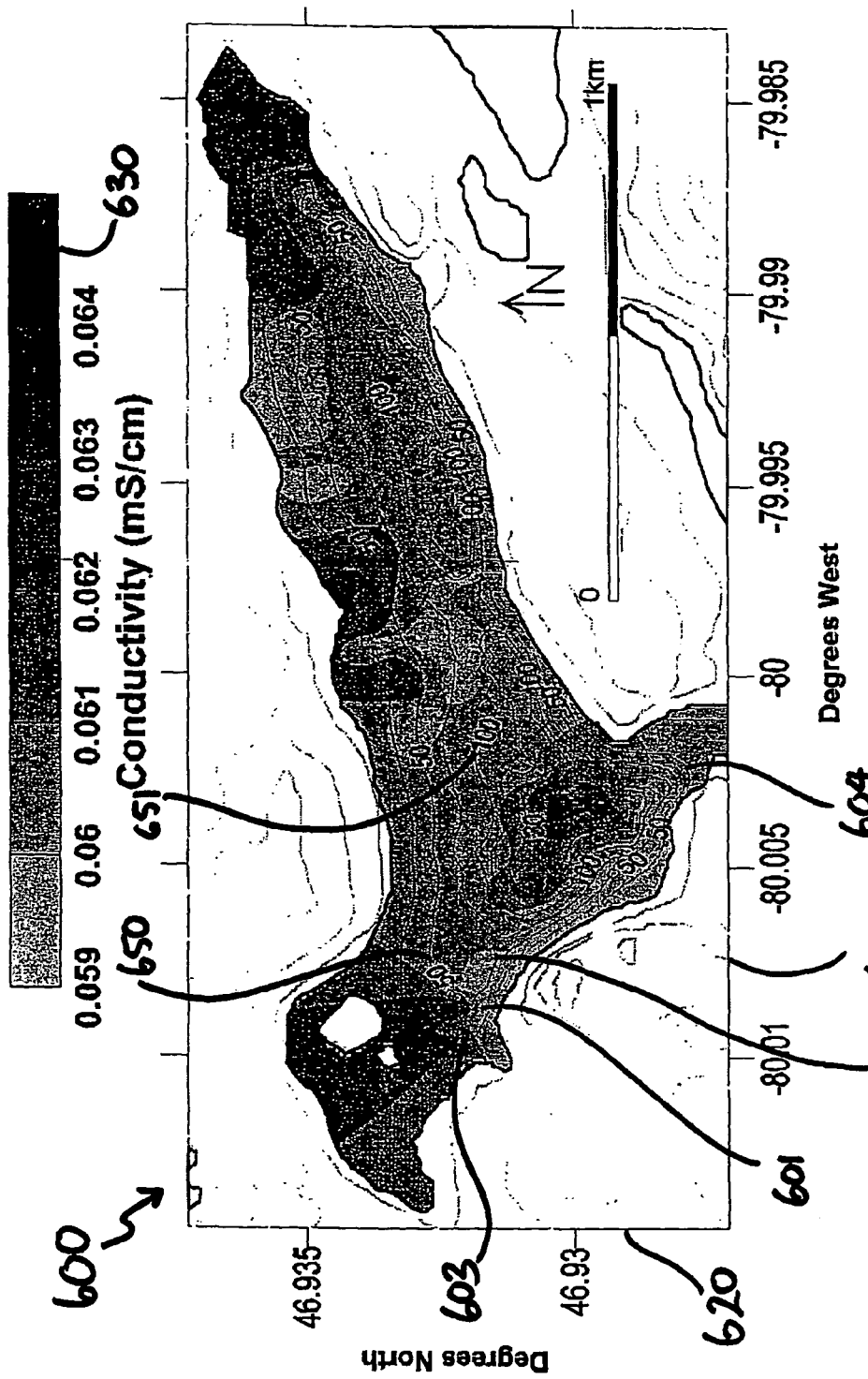
FIG. 6 shows another part of the same lake as that shown in FIG. 4, bottom depth contours are mapped against conductivity contours.

FIGS. 4 to 6 show exemplary maps, which can be produced using a system, and method as described above. FIGS. 4 and 5 show portions of Lake Temagami, which is a lake of around 70 kilometers in length located in northern Ontario, Canada. FIG. 6 shows a portion of Cross Bay, which is located on Lake Temagami.

Turning firstly to FIG. 4 which shows bottom depth contours verses dissolved oxygen contours for a segment of Lake Temagami around Temagami Island. In this map 400 (and FIGS. 5 and 6) the horizontal axis 410 represents longitude in degrees west, and the vertical axes 420 represents latitude in degrees north. The line of crosses 401 represents the path taken by the tow vehicle whilst the sled is taking measurements of the water quality variable. Each cross eg. 402 represents a measurement point along the path of the tow craft. The total length of the track shown in FIG. 4 is around 15 kilometers.

The depth contours of the body of water are shown by the lines e.g. 403 and 404 with the 20, 40, 50, 60 and 80 foot depth contours being labelled eg. 421, 440, 450 and 460 respectively. Land masses, such as the lake shore and islands eg. Temagami Island 475 are shown as white regions without topographical contours.

The shading from light to dark grey which is overlayed onto this topographical information of the lake bottom represents dissolved oxygen as a percentage of saturation with air. Scale 409 shows the percentage saturation which each shade of grey represents. In an alternative embodiment the shades of grey can be represented in colour or as a second set of contours overlain on the topographic contour information.

The dissolved oxygen contours between the adjacent measurement paths are interpolated values calculated by mapping software. In parts of the map in which only a single path is present the dissolved oxygen contours are only accurate in the immediate vicinity of the path as the measurements taken by the sled are only representative of the variable values at the point at which the measurement is taken rather than over some larger volume. Thus, in places of interest such as that shown in FIG. 5 a large number of measurements are taken in a small area to build up an accurate picture of the measured physical or chemical variable(s) in the region of interest.

Turning now to FIG. 5 which shows a close up view 500 of a small dissolved oxygen anomaly 499 located at latitude 46.96° and longitude 80.03° in FIG. 4.

In FIG. 5 the points at which measurements were taken using the measuring device are marked with crosses 501 and the dissolved oxygen contours are mapped over the topographical contours eg. 510, 520 as previously described in connection with FIG. 4. From FIG. 5 it can be determined that a correlation exists in this position between depth and dissolved oxygen. This suggests that ground water is erupting in the deepest part of the lake in this immediate area.

FIG. 6 shows a similar map to that shown in FIGS. 4 and 5. However, FIG. 6 shows a segment of Cross Bay, and plots topographic contours, against conductivity contours measured in millisiemens. Again the horizontal axis 610 represents longitude in degrees west, and the vertical axes 620 represents latitude in degrees north. The line of crosses 601 represents the path taken by the tow vehicle whilst the sled is taking measurements of the water quality variable. Each cross eg. 602 represents a measurement point along the path of the tow craft. Depth contours of the body of water are shown by the lines eg. 603 and 604 with the 50 and 100 foot depth contours being labelled eg. 650 and 651 respectively. However, the land masses, such as the lake shore and islands are shown as white regions with topographical contours in this example.

The scale 630 shows the correlation between shading and conductivity. This map 600 shows that there is not a strong correlation between depth and conductivity in this lake.

As will be appreciated by a person skilled in the art various analyses can be performed using graphs of different water quality variables or measures of physical variables. For example, from FIG. 5 it may be ascertained that in this part of the lake there is an erupting ground water supply with lower concentration of dissolved oxygen than in the surrounding lake water.

Embodiments of the present invention can be used to take measurements and create maps of bodies of standing surface water such as lakes, ponds, lagoons, harbours, tidal estuaries and, with various modifications the continental shelf Within such bodies of water the invention can be used to identity such occurrences as sources of erupting ground water, sources of contaminants or pollutants, and trace their spread in three dimensions throughout the body of water; identify chemical reactions produced by such contaminants introduced into the water. Embodiments of the invention can be used to identify circulation patterns in the standing body of water; the flow rate and volume of contaminants introduced into the body of water and locate sources of contaminants in the water.

Embodiments of the system and method as described above is particularly useful in environmental assessment monitoring and surveying. In large bodies of water such a system and method may be used to determine water quality over the entire body in a quick and efficient manner. Furthermore, such a system may be advantageously employed in mineral exploration. For example, ground water traversing an unknown ore deposit will pick up a distinct chemical signature which may be identified, and the source detected through subsequent ground water discharge into a standing body of water. In combination with geological surveying and other operations the location of the ore deposit can be determined. An embodiment of the system and method could also be used to located sources of fresh ground-water erupting from the continental shelf Such sources of groundwater may then be tapped to supply fresh water to remote costal communities near-by. will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

The invention claimed is:

1. A method for identifying groundwater introduced into a body of water, said method including the steps of:
   providing dynamic measurement means for taking in situ measurements of at least one physical or chemical variable;
   towing said measurement means in said body of water at a predetermined depth whilst taking in situ measurements of least one physical or chemical variable, at least periodically, and generating measurement data;
   determining the location of the measurement means when an in situ measurement of a physical or chemical variable is made and generating corresponding location data; and
   identifying groundwater within the body of water on the basis of the measurement data and location data.

2. A method as claimed in claim 1 which includes the additional-step of:
   controlling the depth of the measurement means in said body of water whilst towing said measurement means.

3. A method as claimed in claim 2 which includes the additional step of:
  detecting obstacles in a region adjacent to said measurement means; and
  wherein the step of controlling the depth of said measurement means is performed in response to detected obstacles.

4. A method as claimed in claim 3 in which the step of, detecting obstacles in a region adjacent to said measurement means, includes the sub-steps of:
  providing image capture means on said measurement means, adapted to generate a sequence of images of a region adjacent to said measurement means; and
  visually detecting said obstacles from said sequence of images.

5. A method as claimed in claim 2 wherein the predetermined depth is determined relative to a bottom of the body of water.

6. A method as claimed in claim 1 wherein said measurement means includes water intake means configured to collect water from said body of water and wherein said method includes the additional step of:
  collecting at least one water sample from said body of water through said water intake means.

7. A method as claimed in claim 1 wherein a plurality of physical or chemical variables are measured by said measurement means.

8. A method as claimed in claim 1 wherein at least one physical or chemical variable measured by the measurement means is selected from a list including the following physical variables:
  water depth, water temperature, conductivity, and water turbidity, pH, dissolved oxygen, dissolved chloride, oxidation-reduction potential (ORP), soluble nitrate, ammonia, dissolved gases or chlorophyll A.

9. A method as claimed in claim 1 including measuring a level of dissolved gas in the water and at least one other physical or chemical variable that is capable of distinguishing between the emerging groundwater and the water in a body of water that surrounds the emerging groundwater.

10. The method of claim 1 wherein a plurality of physical or chemical variables is measured in situ by the dynamic measurement means, and the plurality of physical or chemical variables includes at least one dissolved oxygen and oxidation-reduction potential (ORP).

11. The method of claim 1 wherein the step of determining the location of the measurement means is performed substantially simultaneously with the taking of an in situ measurement of a physical or chemical variable.

12. The method of claim 1 further including:
  taking in situ measurements of least one physical or chemical variable indicative of the occurrence of a chemical reaction caused by the interaction of the groundwater with the body of water.

13. The method of claim 12 further including:
  determining the areal geometry of a plume of groundwater within the body of water on the basis of said measurements of least one physical or chemical variable indicative of the occurrence of a chemical reaction caused by the interaction of the groundwater with the body of water.

14. The method of claim 12 further including:
  identifying a site of emergence of groundwater into the body of water on the basis of said measurements of least one physical or chemical variable.

15. The method of claim 1 which further includes:
  identifying one or more contaminants contained in the groundwater on the basis of the in situ measurements of least one physical or chemical variable.

16. A method of mapping groundwater introduced into a body of water, said method including the steps of:
  providing dynamic measurement means the for making in situ measurements of at least one physical or chemical variable indicative of groundwater in contrast to said body's water;
  towing said measurement means in said body of water at a predetermined depth whilst taking in situ measurements of said at least one physical or chemical variable, at least periodically, and generating measurement data;
  determining the location of the measurement means at a time of taking said measurements of a physical or chemical variable and generating corresponding location data; and
  generating a map representative of the distribution of at least one physical and/or chemical variable indicative of groundwater within said body of water on the basis of the location and measurement data to illustrate said groundwater within the body of water.

17. A method as claimed in claim 16 including the additional step of:
  determining the depth of the measurement means when measuring said at least one other physical or chemical variable, and generating measurement depth data, and wherein said map is generated on the basis of the measurement depth data, measurement data and location data.

18. A method as claimed in claim 17 which includes the additional step of:
  controlling the depth of the measurement means in said body of water whilst towing said measurement means.

19. A method as claimed in claim 18 which includes the additional step of:
  detecting obstacles in a region adjacent to said measurement means; and
  wherein the step of controlling the depth of said measurement means is performed in response to detected obstacles.

20. A method as claimed in claim 19 in which the step of, detecting obstacles in a region adjacent to said measurement means, includes the sub-steps of:
  providing image capture means on said measurement means, adapted to generate a sequence of images of a region adjacent to said measurement means; and
  visually detecting said obstacles from said sequence of images.

21. A method as claimed in claim 16 in which said measurement means includes water intake means configured to collect water from said body of water and wherein said method includes the additional step of:
  collecting at least one water sample from said body of water through said water intake means.

22. A method as claimed in claim 16 wherein the predetermined depth is determined relative to a bottom of the body of water.

23. A method as claimed in claim 16 wherein a plurality of physical or chemical variables are measured by said measurement means.

24. A method as claimed in claim 16 wherein at least one physical or chemical variable measured by the measurement means is selected from a list including the following:
  water depth, water temperature, conductivity, water turbidity, pH, dissolved oxygen, dissolved chloride, oxidation-reduction potential (ORP), soluble nitrate, ammonia, dissolved gases or chlorophyll A.

25. A method as claimed in claim 16 including taking in situ measurements of a level of dissolved gas in the water and at least one other physical or chemical variable that is capable of distinguishing between the emerging groundwater and the water in a body of water that surrounds the emerging groundwater.

26. A method as claimed in claim 16 in which the map represents depth contours of a body of water and the distribution at least one other physical and/or chemical variable within said body of water to thereby illustrate a site of emerging groundwater within the body of water.

27. A method as claimed in claim 26 wherein the map represents the at least one distribution of a physical or chemical variable as a plurality of contours.

28. A method as claimed in claim 26 wherein the depth contours of a body of water represent one of the following depths:
   the depth of the body of water at a location of the measurement means at a time of taking said measurements of a physical or chemical variable;
   a depth at which a measurement of a physical or chemical variable is made.

29. A system for identifying groundwater within a body of water, said system including:
   measurement means configured to take in situ measurements of at least one physical or chemical variable, including at least one variable indicative of a level of dissolved gas in the water, wherein in use said measurement means is configured to be towed in said body of water at a predetermined depth whilst measuring, at least periodically, said at least one physical or chemical variable to generate measurement data;
   location means configured to determine the location of the measurement means at a time of making an in situ measurement of a one physical or chemical variable to generate location data corresponding to the in situ measurement; and
   data storage means configured to store said measurement data and location data.

30. A system as claimed in claim 29 which further includes depth control means configured to control the depth of the measurement means while said measurement means is being towed.

31. A system as claimed in claim 29 further including image capture means adapted to provide a sequence of images of a region of the body of water adjacent the measurement means.

32. A system as claimed in claim 29 which further includes a water inlet means, mounted on said measurement means, configured to allow collection one or more water samples from the body of water.

33. A system as claimed in claim 29 wherein said at least one measurement means is configured to measure one or more of the following physical variables:
   water depth, water temperature, conductivity, water turbidity.

34. A system as claimed in claim 29 wherein said at least one sensor is configured to measure one or more of the following chemical variables:
   pH, dissolved oxygen, dissolved chloride, oxidation-reduction potential (ORP), soluble nitrate, ammonia, dissolved gases or chlorophyll A.

35. The system of claim 29, wherein the measurement means is configured to additionally take in situ measurements of least one additional physical or chemical variable that is capable of distinguishing between the emerging groundwater and the water in body of water that surrounds said emerging groundwater.

36. A method of mapping at least one physical or chemical variable in body of water, said method including the steps of:
   providing dynamic measurement means configured to measure the at least one physical or chemical variable in situ;
   towing said measurement means in said body of water at a predetermined depth whilst taking in situ measurements of said at least one physical or chemical variable, at least periodically, and generating measurement data;
   determining the location of the measurement means at a time of taking said measurements of a physical or chemical variable and generating corresponding location data; and
   generating a map representative of the distribution of the at least one physical or chemical variable within said body of water on the basis of the location and measurement data, said map representing a plurality of contour sets representative of the distribution of plurality of respective plurality of physical or chemical variables including depth contours of the body of water and the distribution of the at least one other physical or chemical variable within said body of water.

* * * * *

UNITED STATES PATENT AND TRADEMARK OFFICE
CERTIFICATE OF CORRECTION

PATENT NO.       : 7,296,464 B2
APPLICATION NO.  : 10/480072
DATED            : November 20, 2007
INVENTOR(S)      : P. B. Hostetler It is certified that error appears in the above-identified patent and that said Letters Patent is hereby corrected as shown below:

On the Title Page,
Item (57)      Abstract           after "measurements of" insert --at--

Col. 10        line 65            "additional-step" should read --additional step--
               (Claim 2)

Col. 11        line 52            "of least one" should read --of at least one--
               (Claim 12)

Col. 11        line 60            "of least one" should read --of at least one--
               (Claim 13)

Col. 11        lines 66-67        "of least one" should read --of at least one--
               (Claim 14)

Col. 12        lines 3-4          "of least one" should read --of at least one--
               (Claim 15)

Col. 13        line 11            "of least one" should read --of at least one--
               (Claim 26)

Col. 13        line 37            "a one physical" should read --of said at least one
               (Claim 29)         physical--

Col. 14        line 3             "collection one or more" should read --collection of
               (Claim 32)         one or more--

Col. 14        line 22            "in body of water" should read --in the body of water--
               (Claim 35)

UNITED STATES PATENT AND TRADEMARK OFFICE
CERTIFICATE OF CORRECTION

PATENT NO. : 7,296,464 B2
APPLICATION NO. : 10/480072
DATED : November 20, 2007
INVENTOR(S) : P. B. Hostetler It is certified that error appears in the above-identified patent and that said Letters Patent is hereby corrected as shown below:

Col. 14     lines 43-44     "distribution of plurality of respective plurality of"
             (Claim 36)       should read --distribution of a respective plurality of--

Signed and Sealed this

Fifth Day of August, 2008

JON W. DUDAS
*Director of the United States Patent and Trademark Office*